US011832796B2

(12) United States Patent
Suyama

(10) Patent No.: US 11,832,796 B2
(45) Date of Patent: Dec. 5, 2023

(54) IMAGING MODULE, ENDOSCOPE SYSTEM, AND IMAGING MODULE MANUFACTURING METHOD

(71) Applicant: OLYMPUS CORPORATION, Tokyo (JP)

(72) Inventor: Takuro Suyama, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/957,305

(22) Filed: Sep. 30, 2022

(65) Prior Publication Data

US 2023/0029662 A1 Feb. 2, 2023

Related U.S. Application Data

(63) Continuation of application No. PCT/JP2020/018702, filed on May 8, 2020.

(51) Int. Cl.
*A61B 1/04* (2006.01)
*A61B 1/00* (2006.01)
*A61B 1/05* (2006.01)

(52) U.S. Cl.
CPC ............ *A61B 1/04* (2013.01); *A61B 1/00009* (2013.01); *A61B 1/00096* (2013.01); *A61B 1/051* (2013.01); *A61B 1/0011* (2013.01)

(58) Field of Classification Search
CPC ............ A61B 1/00009; A61B 1/00096; A61B 1/0011; A61B 1/04; A61B 1/051
See application file for complete search history.

(56) References Cited

U.S. PATENT DOCUMENTS

| 9,899,442 B2 * | 2/2018 | Katkar | H01L 24/85 |
| 11,619,772 B2 * | 4/2023 | Sasaki | H01L 27/14627 |
| | | | 348/311 |

(Continued)

FOREIGN PATENT DOCUMENTS

| JP | 2009-240634 A | 10/2009 |
| JP | 2010-147200 A | 7/2010 |

(Continued)

OTHER PUBLICATIONS

International Search Report dated Jul. 21, 2020 received in PCT/JP2020/018702.

*Primary Examiner* — Kevin K Pyo
(74) *Attorney, Agent, or Firm* — Scully, Scott, Murphy & Presser, P.C.

(57) ABSTRACT

An imaging module includes an imager having an optical member on a light receiving surface, an electronic component having a front surface facing the same direction as the one to which an incidence surface of the optical member faces, a resin portion that has a first surface flush with the incidence surface of the optical member and the front surface of the electronic component, and a second surface that is a surface on a side opposite to the first surface while having the imager and the electronic component being embedded therein such that the incidence surface and the front surface are exposed to the first surface, an external connection terminal provided on the second surface, and a through wiring that extends through the resin portion to connect at least one of the imager and the electronic component with the external connection terminal.

17 Claims, 15 Drawing Sheets

(56) References Cited

U.S. PATENT DOCUMENTS

2009/0244259 A1 10/2009 Kojima et al.
2018/0211989 A1 7/2018 Hogyoku et al.
2020/0344386 A1 10/2020 Yamamoto et al.

FOREIGN PATENT DOCUMENTS

| JP | 2019-136387 A | 8/2019 |
| WO | 2017/014072 A1 | 1/2017 |
| WO | 2019/138440 A1 | 7/2019 |

\* cited by examiner

IMAGING MODULE, ENDOSCOPE SYSTEM, AND IMAGING MODULE MANUFACTURING METHOD

CROSS REFERENCE TO RELATED APPLICATION

This application is a continuation of International Patent Application No. PCT/JP2020/018702, having an international filing date of May 8, 2020, which designated the United States, the entirety of which is incorporated herein by reference.

BACKGROUND

An imaging module having an image sensor or the like mounted on a mount substrate has been conventionally known. For example, Japanese Patent Laid-Open No. 2010-147200 discloses that the image sensor mounted on the substrate is enclosed with an outer frame, and sealed with a resin material. Japanese Patent Laid-Open No. 2009-240634 discloses the capsule type endoscope in which the camera module derived from those integrally formed in a wafer-like state is mounted on the mount substrate.

SUMMARY

In accordance with one of some aspect, there is provided an imaging module, comprising:
an imager having an optical member on a light receiving surface;
an electronic component having a front surface, the front surface and an incidence surface of the optical member facing a same direction;
a resin portion that has a first surface flush with the incidence surface of the optical member and the front surface of the electronic component, and a second surface that is a surface on a side opposite to the first surface, the imager and the electronic component being embedded in the resin portion such that the incidence surface and the front surface are exposed to the first surface;
an external connection terminal provided on the second surface; and
a through wiring that extends through the resin portion to connect at least one of the imager and the electronic component with the external connection terminal.

In accordance with one of some aspect, there is provided an endoscope system including an imaging module and a processor that processes image data acquired by the imaging module, wherein:
the imaging module includes:
an imager having an optical member on a light receiving surface;
an electronic component having a front surface, the front surface and an incidence surface of the optical member facing a same direction;
a resin portion that has a first surface flush with the incidence surface of the optical member and the front surface of the electronic component, and a second surface that is a surface on a side opposite to the first surface, the imager and the electronic component being embedded in the resin portion such that the incidence surface and the front surface are exposed to the first surface;
an external connection terminal provided on the second surface; and
a through wiring that extends through the resin portion to connect at least one of the imager and the electronic component with the external connection terminal.

In accordance with one of some aspect, there is provided an imaging module manufacturing method comprising:
a mounting step of mounting an imager and an electronic component on a support substrate such that both an incidence surface of the imager and a front surface of the electronic component face the support substrate;
a sealing step of supplying a resin onto the support substrate to seal the imager and the electronic component to form a resin portion having a first surface and a second surface on a side opposite to the first surface, the first surface being flush with the incidence surface of the imager and the front surface of the electronic component; and
a removing step of removing the support substrate.

DESCRIPTION OF EXEMPLARY EMBODIMENTS

Figure 1:
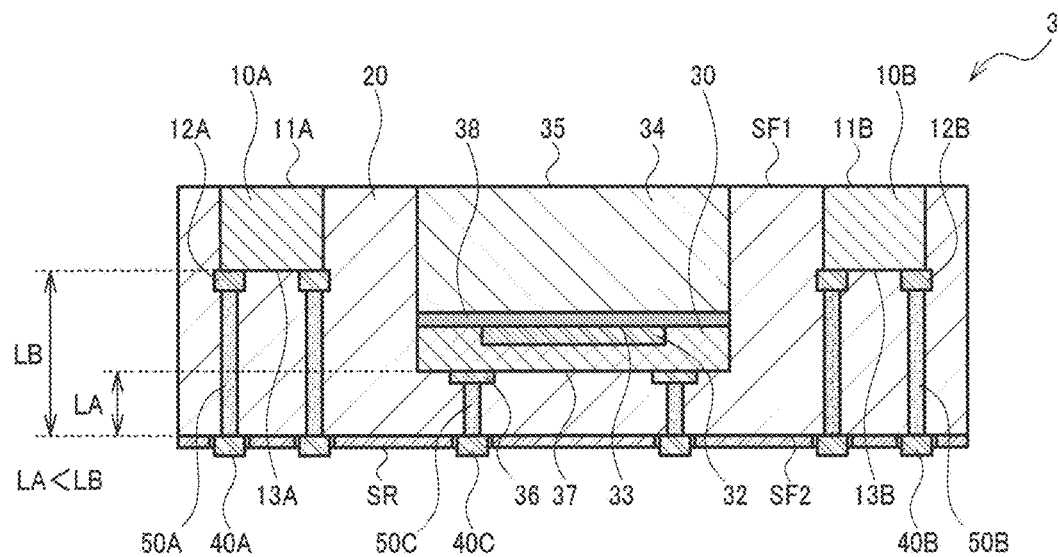
FIG. 1 illustrates a configuration example of an imaging module.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

Embodiments will be described below. The embodiments to be described herein are not intended to unreasonably limit the content described in the claims. All configurations to be described in the embodiments are not necessarily regarded as being essential components of the disclosure.

1. Imaging Module

FIG. 1 is a sectional view of a configuration example of an imaging module 3 according to an embodiment. More specifically, FIG. 1 is a sectional view of the imaging module 3 in a plane parallel to an optical axis of the imaging module 3 while being orthogonal to a light receiving surface 33 of an imaging element 32 of an imager 30 as described later. This applies to the drawings of FIGS. 2 to 8B, FIGS. 10 to 14, and FIGS. 16A, 16B hereinafter. The imaging module 3 in FIG. 1 includes electronic components 10A, 10B (hereinafter, as appropriate, simply referred to as electronic components 10 collectively), a resin portion 20, the imager 30, and external connection terminals 40A, 40B, 40C (hereinafter, as appropriate, simply referred to as external connection terminals 40 collectively). The imager 30 includes an optical member 34. The electronic components 10 have front surfaces 11A, 11B (hereinafter, as appropriate, simply referred to as front surfaces 11 collectively) each facing the same direction as that of an incidence surface 35 of the optical member 34. The resin portion 20 has a first surface SF1, and a second surface SF2 on the side opposite to the first surface SF1. The imager 30 and the electronic components 10A, 10B are embedded in the resin portion 20 such that the incidence surface 35 and the front surfaces 11A, 11B are exposed from the first surface SF1. The first surface SF1 is flush with the incidence surface 35 and the front surfaces 11A, 11B of the electronic components 10A, 10B. The external connection terminals 40 are provided on the second surface SF2.

In the following description, the drawings based on the embodiments are provided for illustrative purpose. Accordingly, it should be noted that the relationship between thickness and width of each component, and a thickness ratio and a relative angle of each component are different from those of the actual component. The dimensional relationship and the ratio in each of the drawings may also be partially different. Illustration of a part of the components may be omitted.

The imager 30 serves to output a signal indicating image data captured by the imaging element 32 to be described later to the outside. The imager 30 includes the imaging element 32, the optical member 34, and an imager terminal 36. The imager 30 may be formed by executing the process of Chip Size Package, or Wafer Level Chip Size Package (WLCSP), for example. The imager 30 may be referred to as an image sensor, or a camera module. A structure of the imager 30 of the imaging module 3 is not limited to the one as described above, but may be variously modified. For example, the single imaging module 3 may be constituted by two or more imagers 30.

The imaging element 32 serves to convert information of light incident on the light receiving surface 33 into image data. The imaging element 32 is formed as a semiconductor element, for example, a Charge-Coupled Device (CCD), or a Complementary Metal-Oxide-Semiconductor (CMOS) sensor. The imaging element may also be formed as other devices.

The optical member 34 serves to protect the imaging element 32 and to guide the light thereto. For example, the imaging element 32 and the optical member 34 are bonded using a transparent adhesive 38 such that the light incident on the incidence surface 35 of the optical member 34 is further made incident on the light receiving surface 33 of the imaging element 32. The optical member 34 may be formed as a cover glass which allows light to travel straight. However, the optical member 34 may also be formed as a lens for condensing light, a prism for refracting light, or an optical system unit as a combination of multiple kinds of those elements.

The imager terminal 36 serves to perform electric input/output operations between the imaging element 32 and an external device. For example, output of a signal from the imaging element 32, or input of a control signal from the external device may be performed through the imager terminal 36. The signal output from the imaging element 32 may be a pixel signal, for example. The imager terminal 36 is formed on a surface opposite to the surface on which the imaging element 32 is provided. The imager terminal 36 may be formed as a spherical solder bump, a gold stud bump, a pad using such surface-forming material as Au, Cu, and Al for connection, or the conductive paste. The imager terminal may also be formed using any other material or into any other shape.

The electronic component 10 serves to assist a function of the imaging module 3, for example, and may be formed as a light emitting element for emitting light to an object to be captured by the imager 30, for example. The electronic component may also be formed as other elements such as an active element and a passive element. The active element is an element for amplifying and controlling an electric signal based on supplied electric power, for example, a transistor, a diode, or a sensor. The passive element is an element which does not perform the active operations described above, for example, a resistance or a capacitor. The structure of the electric component of the imaging module 3 is not limited to the one as described above, but may be variously modified. For example, a single unit of the imaging module 3 may be constituted by a single unit of the electronic component 10, or three or more units of the electronic components 10.

Electronic component terminals 12A, 12B (hereinafter, as appropriate, simply referred to as electronic component terminals 12 collectively) are terminals for performing electric input/output operations between the electronic components 10A, 10B, and the external device. For example, input of a control signal from the external device, or output of a signal from the electronic component 10 is performed through the electronic component terminal 12. The electronic component terminal 12 is formed as a spherical solder bump or a gold stud bump. Alternatively, a pad or a terminal of the electronic component itself may be used as it is without adding a new terminal to the electronic component 10. The electronic component terminal may be formed using any other material or into any other shape.

The resin portion 20 is a part to be packaged by sealing the imager 30 and the electronic components 10 using a resin material. The resin portion 20 is produced by executing the process of pouring a thermosetting resin into a prescribed mold, for example. The resin portion may also be produced by executing any other process. The thermosetting resin is produced using epoxy resin, for example, as a main material. The thermosetting resin may also be produced using any other resin as the main material. The resin portion 20 may be produced by adding the material other than the resin. This allows the resin portion 20 to protect the imager 30 and the electronic components 10 from the external environment. For example, the external environment may be temperature, humidity, impact or light. For example, addition of the high light shielding material to the main material of the resin portion 20 makes it possible to protect the imager 30 from stray light.

The front surfaces 11A, 11B of the electronic components 10A, 10B face the same direction as that of the incidence surface 35 of the optical member 34 in the imaging module 3. In other words, those surfaces face the same direction as the one orthogonal to those surfaces. The state of facing the same direction includes the state of facing substantially the same direction. The first surface SF1 of the resin portion 20, from which the optical member 34 and the electronic components 10A, 10B are exposed is flush with the incidence surface 35 and the front surfaces 11A, 11B. The flush state represents that no level distance exists between two surfaces. The flush state includes substantially the flush state. The use of a flat support substrate 60 to be described later attains the state where the first surface SF1, the incidence surface 35, and the front surfaces 11 are flush with one another. Such term as flat represents the state in which flatness is within a predetermined range of the predetermined area. For example, the flatness of the support substrate 60 in the area equal to that of the 8-inch wafer (φ200 millimeters) is one micrometer or smaller. As the first surface SF1 including the incidence surface 35 is flat, it is possible to attain mass production of the imaging modules 3 each with high accuracy in an optical axis direction.

The external connection terminal 40 allows connection from outside the resin portion 20 subsequent to formation of the resin portion 20. After being packaged, the imager 30 and the electronic components 10 may be electrically connected to the external device through the external connection terminals 40. The external connection terminal 40 includes a dummy terminal used for an operation other than input/output of electric signals. The external connection terminal 40 is exposed from the second surface SF2 opposite to the first surface SF1 of the resin portion 20. The external connection terminal 40 is formed as the solder bump or the gold stud bump. However, it may be formed using any other material, or into any other shape. The second surface SF2 includes a pattern using the solder resist SR. However, it needs not include such pattern.

Figure 2:
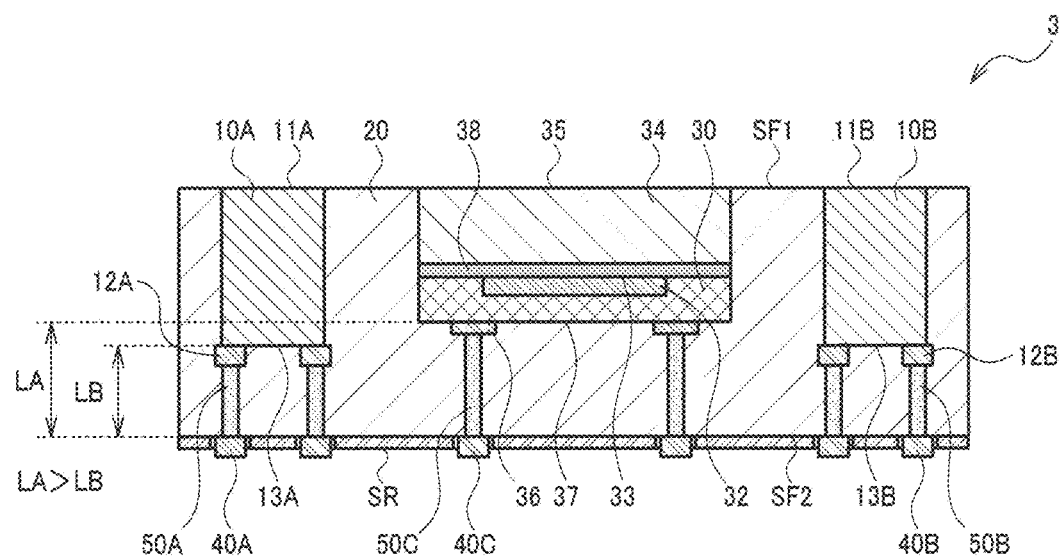
FIG. 2 illustrates a modification of the imaging module.

Referring to the imaging module 3 in FIG. 1, a distance between the second surface SF2 of the resin portion 20 and a surface 37 of the imager 30 which faces the second surface SF2 is defined as LA, and a distance between the second surface SF2 of the resin portion 20 and each of surfaces 13A, 13B (hereinafter, as appropriate, referred to as surfaces 13 collectively) of the electronic components 10A, 10B which face the second surface SF2 is defined as LB. In this case as illustrated in FIG. 1, the relationship of LB>LA is established. That is, as FIG. 1 illustrates, the distance from the second surface SF2 of the resin portion 20 to each surface of the electronic components 10 which faces the second surface SF2 is longer than the distance from the second surface SF2 to the surface of the imager 30 which faces the second surface SF2. Meanwhile, it is possible to establish the relationship of LA>LB as illustrated in FIG. 2. Specifically, referring to FIG. 2, the distance from the second surface SF2 of the resin portion 20 to the surface of the imager 30 which faces the second surface SF2 is longer than the distance from the second surface SF2 to each surface of the electronic components 10 which faces the second surface SF2.

As described above, the imaging module 3 according to the embodiment includes the imager 30, the electronic components 10, the resin portion 20, and the external connection terminals 40. The imager 30 includes the optical member 34. The electronic component 10 has the front surface 11 which faces the same direction as that of the incidence surface 35 of the optical member 34. The resin portion 20 includes the first surface SF1, and the second surface SF2 on a side opposite to the first surface SF1. The imager 30 and the electronic components 10 are embedded in the resin portion 20 such that the incidence surface 35 and the front surfaces 11 are exposed to the first surface SF1. The first surface SF1 is flush with the incidence surface 35 and the front surfaces 11 of the electronic components. The external connection terminals 40 are provided on the second surface SF2.

The imaging module 3 allows the imager 30 and the electronic components 10 to be packaged with no need of mount substrate nor outer frame. This allows the imaging module 3 to be compact, and optimized for application to a leading end of the endoscope. The imaging module 3 according to the embodiment is applicable to the microscope, for example, as well as the endoscope.

The device disclosed in Japanese Patent Laid-Open No. 2009-240634 is configured to simply mount the camera module and the LED on the mount substrate, resulting in the problem of durability against the external environment. The imaging module 3 of the embodiment has the imager 30 and the electronic components 10 sealed and packaged. This makes it possible to improve durability against the external environment.

Furthermore, there may be a problem that a sophisticated technique is necessary for assembly of the imager 30 and the electronic components 10 with a housing at the leading end of the endoscope. As the imaging module 3 of the embodiment has the imager 30 and the electronic components 10 firmly packaged with the resin portion 20, those components may be assembled with the housing in the simplified process.

The dummy electronic component may be included in the electronic component 10. The dummy electronic component is used for operations non-related to the function of the imaging module 3. For example, the dummy electronic component is used in an alignment process as described later.

The first surface SF1 of the imaging module 3 may be differently colored, or have the color density variable to discriminate the resin portion 20, the incidence surface 35, the front surfaces 11, a through wiring 50 to be described later, and a rewiring 52 to be described later from one another. This allows the alignment step to be easily executed.

The imaging module 3 of the embodiment may be provided with through wirings 50A, 50B, 50C (hereinafter, as appropriate, simply referred to as the through wirings 50 collectively), each of which extends through the resin portion 20 to connect the external connection terminal 40 to at least one of the imager 30 and the electronic components 10.

The through wiring 50 serves to electrically connect the external connection terminal 40 to the imager terminal 36 and the electronic component terminals 12, both of which are embedded in the resin portion 20. The through wiring 50 is formed using a conductive material, for example, copper. The through wiring may be formed using other materials, for example, nickel, gold, aluminum, or a solder. The imaging module 3 of the embodiment may be formed even in the case where all terminals of the imager terminal 36 and the electronic component terminals 12 are not connected to the external connection terminals 40.

According to the imaging module 3 having the above-structured through wirings 50, even in the case where the imager 30, the electronic components 10, and the resin portion 20 have different thicknesses, the imager 30 and the electronic components 10 may be packaged collectively conforming to the thickness of the resin portion 20.

The through wiring 50 of the imaging module 3 according to the embodiment may be configured to connect the external connection terminal 40 to the imager 30 or the electronic components 10 selectively in accordance with a distance (LA, LB) from the second surface SF2 to each surface of the imager 30 and the electronic components 10 on a side opposite to the second surface SF2, whichever is longer. For example, as illustrated in FIG. 2, if the distance LA is longer than the distance LB, the imager terminal 36 of the imager 30 and the external connection terminal 40C are connected via the through wiring 50C to form the imaging module 3. As illustrated in FIG. 1, if the distance LB is longer than the distance LA, the electronic component terminals 12A, 12B of the electronic components 10A, 10B, and the external connection terminals 40A, 40B are connected via the through wirings 50A, 50B, respectively to form the imaging module 3. The distance LB in the case of the electronic component 10A may be different from the distance LB in the case of the electronic component 10B. That is, the thickness of the electronic component 10A may be different from the thickness of the electronic component 10B in the thickness direction of the resin portion 20.

The above-configured imaging module 3 allows the component located at a long distance from the second surface SF2 to be brought into conduction with the external connection terminal 40. The through wiring 50 may be formed by executing the plating process.

The imaging module 3 of the embodiment allows at least one of the imager terminal 36 and the electronic component terminals 12 to be exposed to the second surface SF2 to serve as the external connection terminal 40. In other words, the imaging module 3 may be configured to make the distance LA or LB zero (that is, the surface 13 of the electronic component 10 or the surface 37 of the imager 30 becomes flush with the second surface SF2). The imaging module 3 may also be configured to allow the surface 13 of the electronic component 10 or the surface 37 of the imager 30 to protrude from the second surface SF2. In this case, the external connection terminal 40 may be connected to the imager terminal 36 or the electronic component terminal 12, which is not exposed to the second surface SF2, via the through wiring 50. The through wiring 50 needs not be provided for the imager terminal 36 or the electronic component terminal 12, which is exposed from the second surface SF2.

Figure 3:
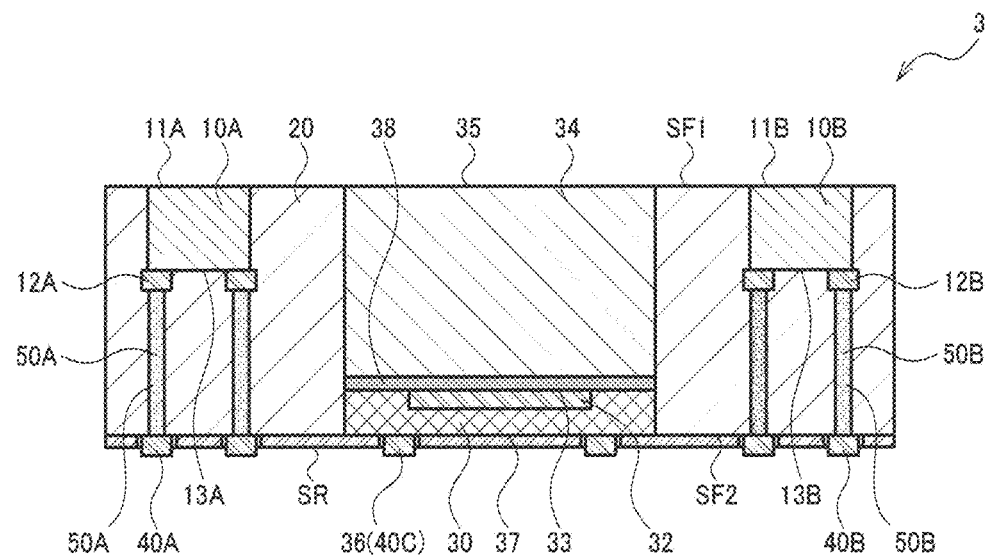
FIG. 3 illustrates a modification of the imaging module.

For example, as illustrated in FIG. 3, the imaging module 3 is configured to expose the imager terminal 36 from the second surface SF2 to serve as the external connection terminal 40. The imaging module 3 as illustrated in FIG. 3 makes the distance LA zero. Although not shown in the drawing, the imaging module 3 may be configured to expose the electronic component terminal 12 from the second surface SF2 to serve as the external connection terminal 40. In this case, the imaging module 3 makes the distance LB zero.

Figure 4:
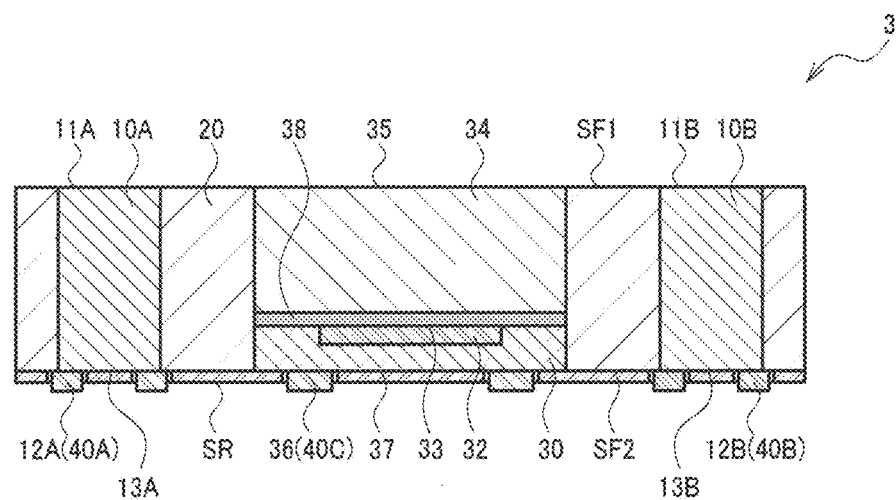
FIG. 4 illustrates a modification of the imaging module.

As FIG. 4 illustrates, for example, the imaging module 3 may be configured to expose the imager terminal 36, and the electronic component terminals 12A, 12B from the second surface SF2 to serve as the external connection terminals 40, respectively. The imaging module 3 as illustrated in FIG. 4 makes each of the distances LA and LB zero.

The imaging module 3 allows the resin portion 20 to have the same thickness as that of the component with the largest thickness. Accordingly, the imaging module 3 may be manufactured to have the minimum possible thickness, and to omit formation of the through wiring 50.

Figure 5:
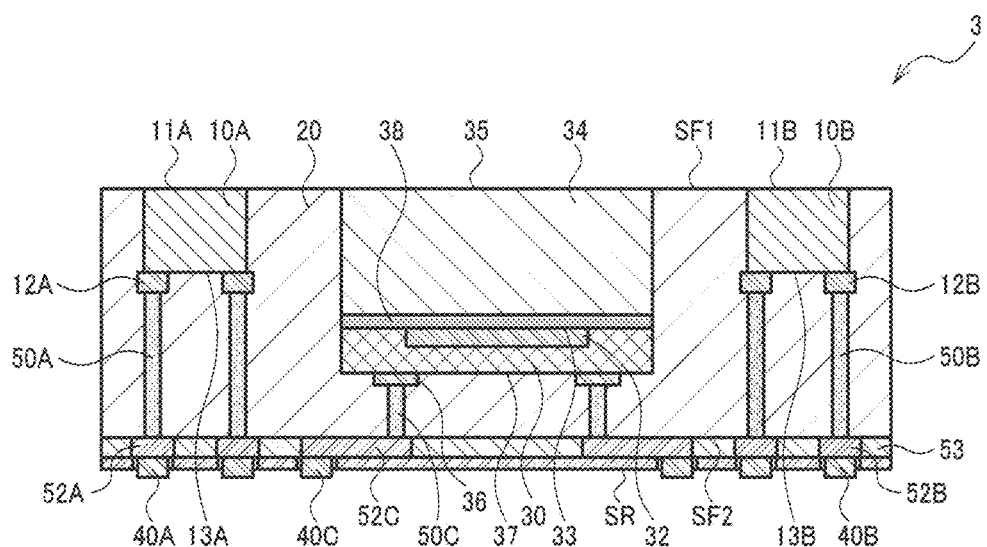
FIG. 5 illustrates a modification of the imaging module.

As the sectional view in FIG. 5 schematically illustrates, the imaging module 3 of the embodiment may be configured to include rewirings 52A, 52B, 52C (hereinafter, as appropriate, simply referred to as rewirings 52 collectively) formed in the second surface SF2 for connecting the external connection terminal 40 to at least one of the imager terminal 36, the electronic component terminals 12, and the through wirings 50. The rewiring 52 is formed to have a predetermined wiring pattern in a planar view of the second surface SF2 seen from below in FIG. 5. The rewiring 52C formed as illustrated in FIG. 5 allows the external connection terminal 40C to be formed at a position different from that of the imager terminal 36 in the planar view of the second surface SF2. Similarly, the rewiring 52A formed as illustrated in FIG. 5 allows the external connection terminal 40A to be formed at a position different from that of the electronic component terminal 12A in the planar view of the second surface SF2. The position different from that of the electronic component terminal 12A refers to the different position in a direction orthogonal to the drawing plane in FIG. 5, for example. This makes it possible to place the external connection terminal 40 on the second surface SF2 at a position which allows easy connection with the signal wiring or the like, resulting in easy mounting. Change in the position of the external connection terminal 40C to the one to which the smaller mechanical load is applied ensures to improve package reliability of the imaging module 3. The imaging module 3 of the embodiment may be configured by forming the rewiring 52 without changing arrangement of the external connection terminal 40. In this case, the layer of the rewiring 52 is formed on the through wiring 50, and the external connection terminal 40 is further provided on the rewiring 52. An insulating layer 53 is formed in the same layer as the rewiring 52. This applies to the configuration to be described later referring to FIGS. 8A and 8B.

2. Method of Manufacturing Imaging Module

Next, a method of manufacturing the imaging module 3 of the embodiment will be described. The imaging module 3 of the embodiment is manufactured by executing the respective steps as illustrated in FIGS. 6A, 6B, 7A, 7B, 8A, and 8B.

Each of FIGS. 6A to 8B is a sectional view illustrating the method of manufacturing the imaging module 3. In the embodiment, multiple imaging modules 3 are arrayed to form the shape like the semiconductor wafer. The substrate may be formed into a polygonal shape such as a quadrangle besides the disc-like shape of the semiconductor wafer. Each of FIGS. 6A to 8B typically illustrates a single unit of module after singulation, and illustration of other modules is omitted. Codes and explanations given to structures and terms similar to those of the above-described imaging module 3 will be omitted.

Figure 6A:
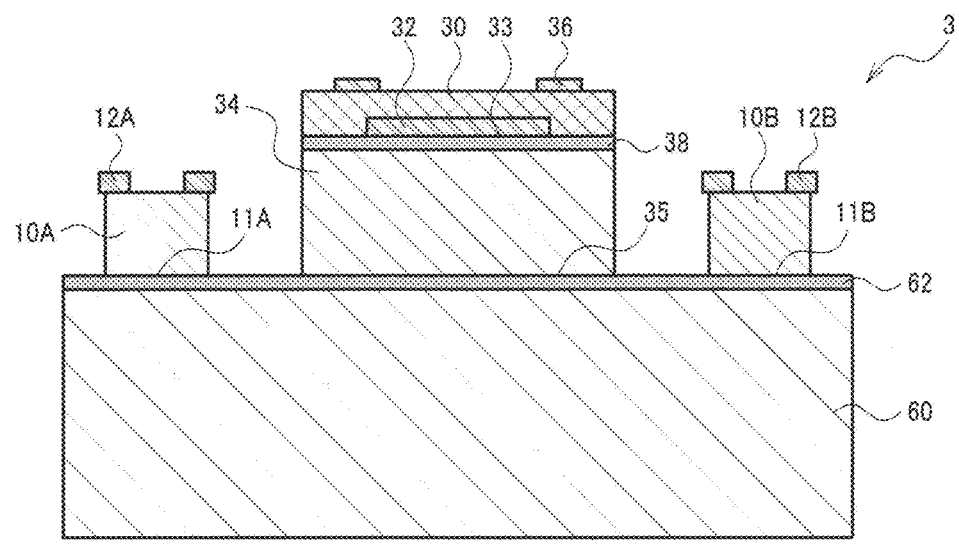
FIGS. 6A and 6B each illustrate a manufacturing process of the imaging module.
Figure 6A:
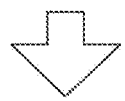

In the first step, as illustrated in FIG. 6A, the imager 30 and the electronic components 10 are mounted onto a temporary bonding member 62 on the support substrate 60. Specifically, the first step is executed by the method as illustrated in FIG. 6A. The first step may be called a mounting step. The first step may be executed by placing the imager 30 and the electronic components 10A, 10B such that the incidence surface 35 of the optical member 34 of the imager 30, and the front surfaces 11A, 11B of the electronic components 10A, 10B come in contact with the temporary bonding member 62. The first step is executed by a component mounter, or may be executed by other devices. FIG. 6A illustrates a configuration example that the single unit of the imaging module 3 is formed by combining the single imager 30 and the two electronic components 10A, 10B. However, the imaging module 3 may be configured by other combinations. The first step may be executed by adding the active element, the passive element, or the dummy electronic component.

The support substrate 60 is an auxiliary member for manufacturing the imaging module 3. In the embodiment, the shape and size of the support substrate 60 are the same as those of a generally employed semiconductor wafer. Executing the wafer dicing process as described later allows collective mass production of the imaging modules 3. The use of the material with high flatness allows production of the support substrate 60. For example, the support substrate 60 is made of glass, or may be made of other materials like silicon.

The temporary bonding member 62 serves to temporarily fix the support substrate 60 and the imaging module 3 in the process of manufacturing the imaging module 3. The temporary bonding member 62 is formed to be as flat as the support substrate 60. For example, a prescribed resin is applied onto the support substrate 60 by a spin coating method to form the temporary bonding member 62. The temporary bonding member 62 may be formed by laminating the sheet material onto the support substrate 60. The material which allows the imaging module 3 to be easily peeled off is used for forming the temporary bonding member 62.

Figure 6B:
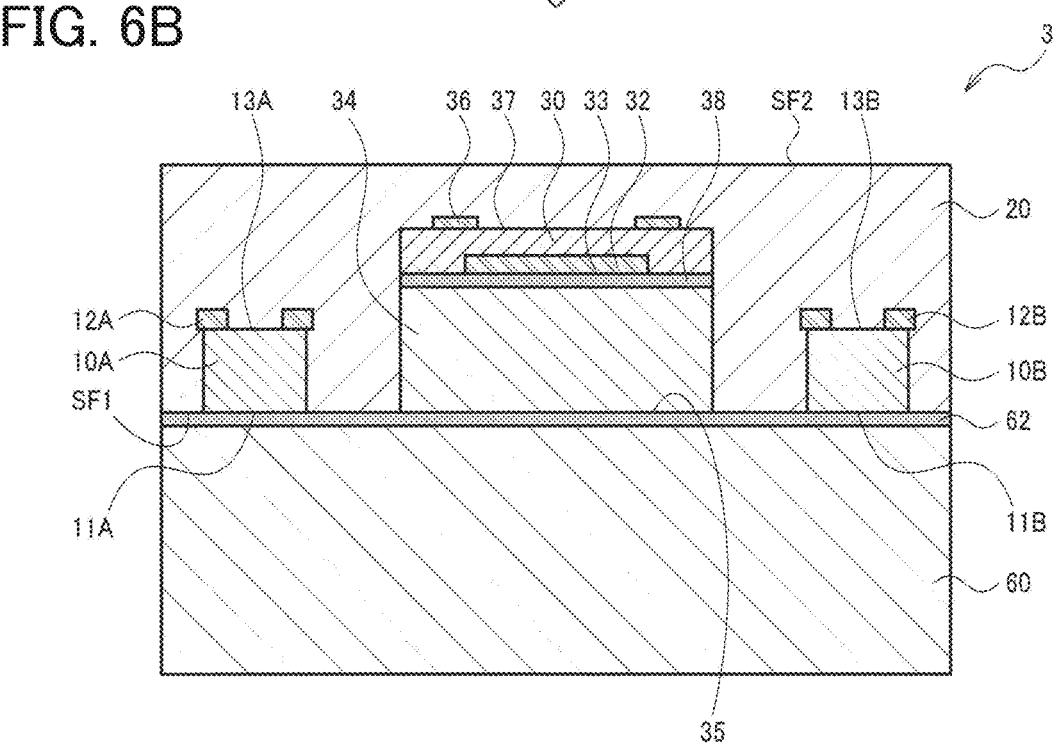
Figure 6B:
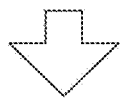

In the second step, as illustrated in FIG. 6B, the resin portion 20 is formed on the temporary bonding member 62. The second step may be called a sealing step. The second step is executed by the mold resin sealing method, or may be executed by other methods. In the second step, the resin portion 20 may be formed to allow any one or all of the imager terminal 36 and the electronic component terminals 12A, 12B to serve as the external connection terminal 40. The terminal which serves as the external connection terminal 40 does not have to be subjected to the third, fourth, and the fifth steps as described later. The resin portion 20 has the first surface SF1 which comes in contact with the temporary bonding member 62, and is flush with the incidence surface 35 and the front surfaces 11. The surface on the side opposite to the first surface SF1 is the second surface SF2.

Figure 7A:
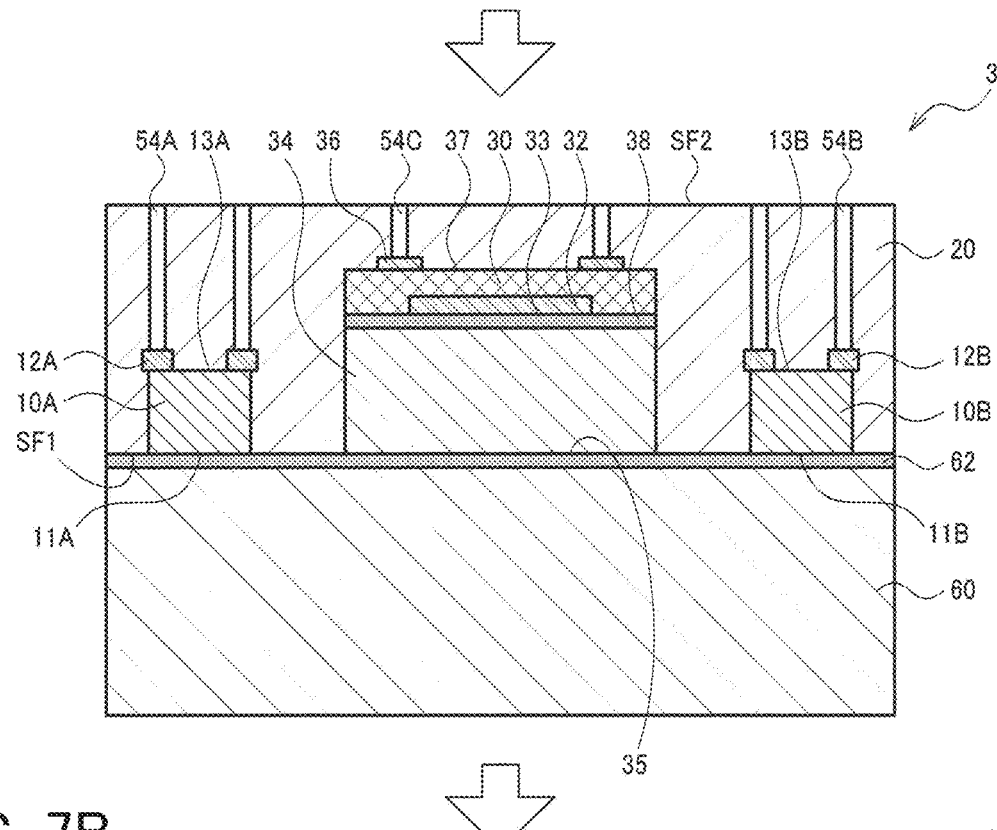
FIGS. 7A and 7B each illustrate the manufacturing process of the imaging module.

In the third step, as illustrated in FIG. 7A, through holes 54A, 54B, 54C (hereinafter, as appropriate, simply referred to as through holes 54 collectively) are formed in the resin portion 20. The third step is executed by forming the through holes 54 from the side of the second surface SF2. The third step is executed by forming the through holes 54 by laser machining. The through holes 54 may also be formed by the etching technique, for example.

The third step may be executed only when any one or all of the imager terminal 36, and the electronic component terminals 12A, 12B are not exposed to the second surface SF2.

Figure 7B:
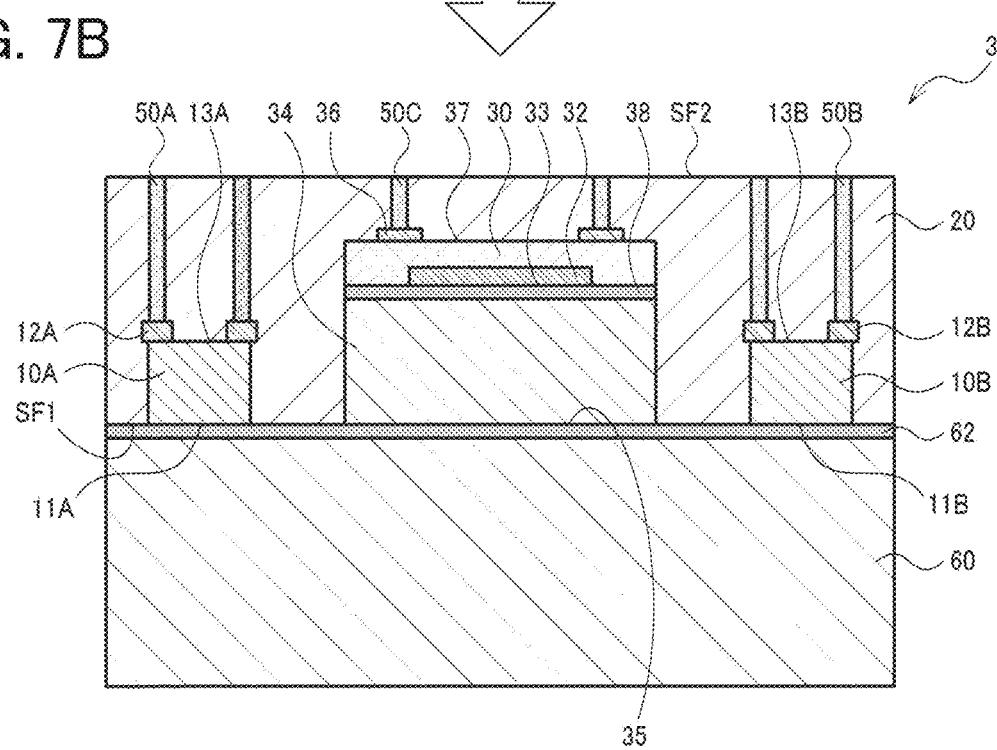

In the fourth step, as illustrated in FIG. 7B, the through wirings 50A, 50B, 50C are formed in the through holes 54 as illustrated in FIG. 7A, respectively. The fourth step by itself, or together with the third step may be called a through wiring forming step. The fourth step is executed by filling the through holes 54 with a conductive material. The fourth step may be executed together with the step of forming the pad on which the external connection terminal 40 is mounted. The fourth step is executed by the electroplating method, or may be executed by other methods. For example, the fourth step may be executed by filling with the conductive paste, or by connecting and mounting a thin and long columnar pin onto the imager terminal 36, and the electronic component terminals 12A, 12B. The fourth step may be executed by the Molded Interconnect Device (MID) technique. The MID technique is utilized for forming the wiring only on the section of the molded resin member irradiated with the prescribed laser light. The MID technique is implemented using the resin forming material which contains a prescribed additive. The fourth step may be executed only in the case where the third step has been executed.

Figure 8A:
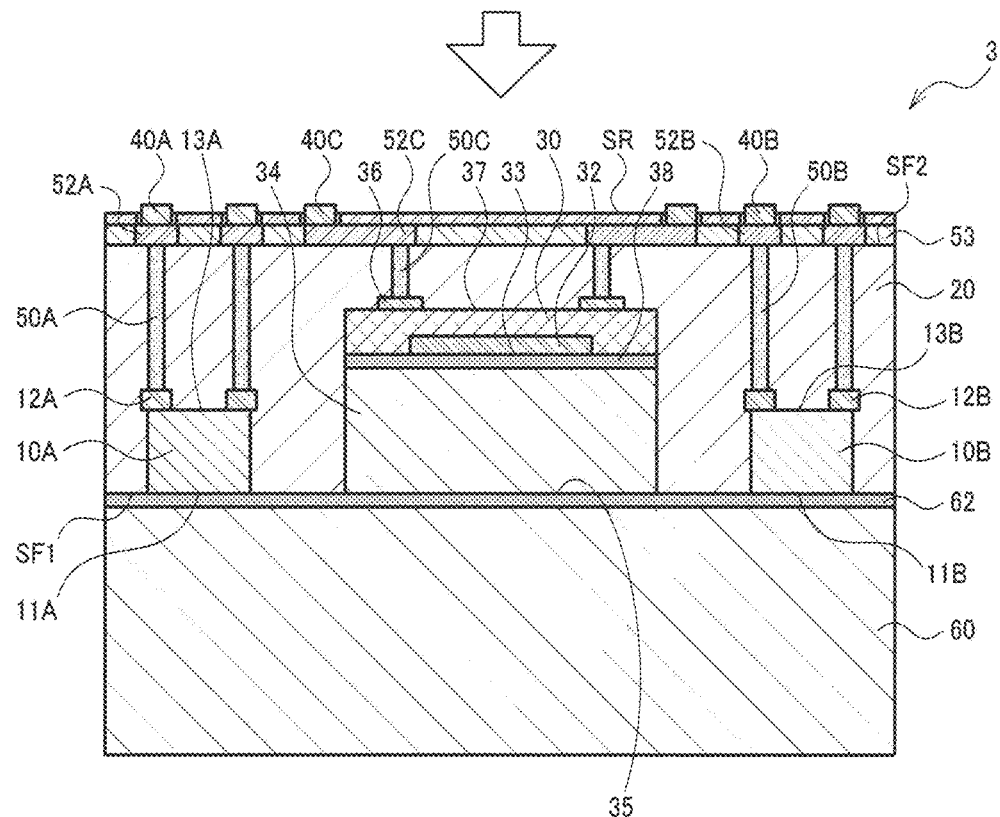
FIGS. 8A and 8B each illustrate the manufacturing process of the imaging module.

In the fifth step, as illustrated in FIG. 8A, the external connection terminals 40A, 40B, 40C are formed. The fifth step is executed by the solder bump forming method, for example, or may be executed by other methods. The solder bump forming method is implemented by the printing technique, or may be implemented by a plating technique or a micro soldering ball mounting technique. The fifth step may be executed together with the step of forming the rewirings 52A, 52B, 52C. If the external connection terminals 40A, 40B, 40C are located at the same positions as the imager terminal 36 and the electronic component terminals 12A, 12B, the step of forming the rewirings 52A, 52B, 52C needs not be executed in the fifth step. The fifth step may be executed together with the step of forming a solder resist SR pattern on the second surface SF2. The fifth step may be executed only in the case where the third and fourth steps have been executed.

Figure 8B:
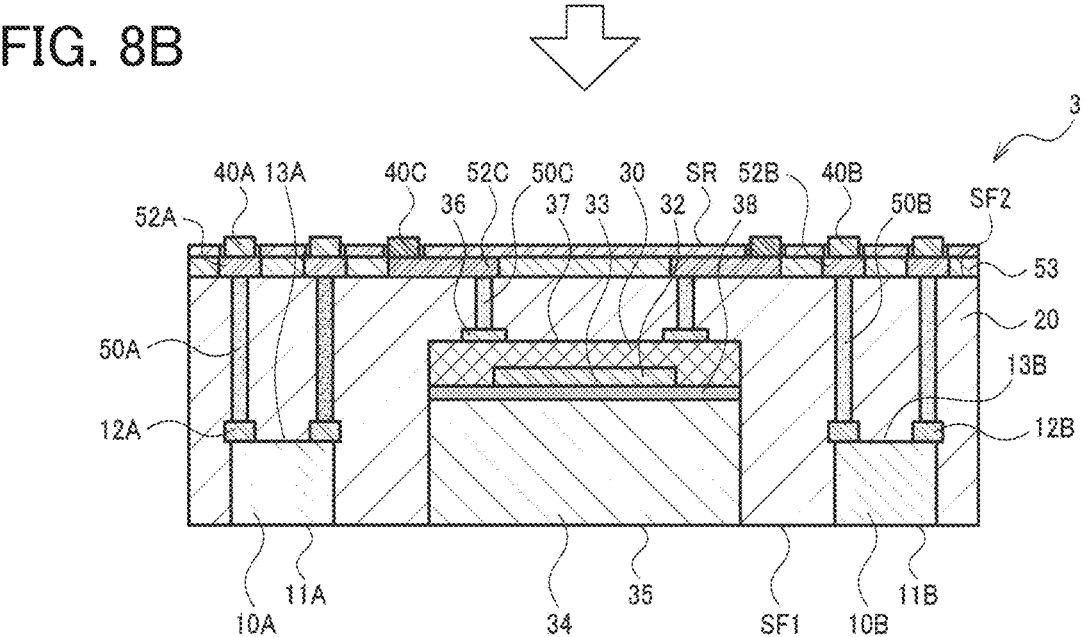

In the sixth step, as illustrated in FIG. 8B, the support substrate 60 and the temporary bonding member 62 are removed from the imaging module 3. The sixth step may be called a removing step. The sixth step is executed by the mechanical peeling-off method, or may be executed by other methods. The step of applying ultraviolet rays and heat to the temporary bonding member 62 may be added to the sixth step.

The sixth step may be executed by generating bubbles from the temporary bonding member 62 to cause self-peeling of the imaging module 3.

A temporary flattening step of temporarily flattening the second surface SF2 may be added to the sixth step. The temporary flattening step may be executed by utilizing a dedicated protective sheet, and a soluble resin. This makes it possible to improve adsorption to the prescribed device at the side on the second surface SF2 to suitably allow peeling of the temporary bonding member 62.

The sixth step is executed by the dedicated device, or may be executed by the same device as the one used in a singulation step to be described later.

As described above, the method of manufacturing the imaging module 3 of the embodiment includes the mounting step, the sealing step, and the removing step. In the mounting step, as illustrated in FIG. 6A, the imager 30 and the electronic components 10 are mounted on the support substrate 60 such that the incidence surface 35 of the imager 30 and the front surfaces 11 of the electronic components 10 face the support substrate 60. In the sealing step, as illustrated in FIG. 6B, the resin is applied onto the support substrate to seal the imager 30 and the electronic components 10. The resultant resin portion 20 has the first surface SF1 flush with the incidence surface 35 and the front surfaces 11, and the second surface SF2 on the side opposite to the first surface SF1. In the removing step, as illustrated in FIG. 8B, the support substrate 60 is removed.

The method of manufacturing the imaging module 3 of the embodiment using no substrate nor outer frame allows the imaging module 3 to be more compact than the one manufactured through the generally employed method. The method allows mass production of the imaging modules 3 in the wafer-like state, each of which has the first surface SF1 flush with the incidence surface 35 and the front surfaces 11.

The through wiring forming process of forming the through wirings 50 in the resin portion 20 may be included for connection with at least one of the imager 30 and the electronic components 10 from the second surface SF2.

Even in the case where each thickness of the imager 30, the electronic components 10, and the resin portion 20 is different, although the thickness of the resin portion 20 is variable depending on the location, the method of manufacturing the imaging module 3 allows those elements to be packaged in the wafer-like state conforming to the thickness of the resin portion 20, which has been set to be the largest.

In the sealing step, as illustrated in FIG. 3 or 4, the resin portion 20 may be formed such that at least one of the imager terminal 36 and the electronic component terminals 12 is exposed from the second surface SF2 to serve as the external connection terminal 40.

The method of manufacturing the imaging module 3 allows the thickness of the resin portion 20 to be set in accordance with that of the component having the largest thickness. This makes it possible to manufacture the imaging module 3 with very small thickness, and to reduce the number of points at which the through wirings 50 are formed, and frequency of forming the through wirings 50.

A step of grinding the resin portion 20 to be executed at arbitrary timing may be included in the method of manufacturing the imaging module 3 of the embodiment.

A step of forming an alignment pattern to be executed at arbitrary timing may be included in the method of manufacturing the imaging module 3 of the embodiment.

A groove forming step of forming a half-cut groove for dicing to be executed at arbitrary timing may be included in the method of manufacturing the imaging module 3 of the embodiment.

The method of manufacturing the imaging module 3 of the embodiment may be implemented by forming the external connection terminal 40 after execution of the singulation step to be described later.

The method of manufacturing the imaging module 3 of the embodiment may be implemented by executing the mounting step, the sealing step, and the removing step to form multiple imaging modules 3 in the wafer-like state collectively, and further executing the additional singulation step for singulation of the multiple imaging modules 3 by the wafer dicing process. Specifically, the singulation step is executed by the method as illustrated in FIGS. 9A and 9B.

Figure 9A:
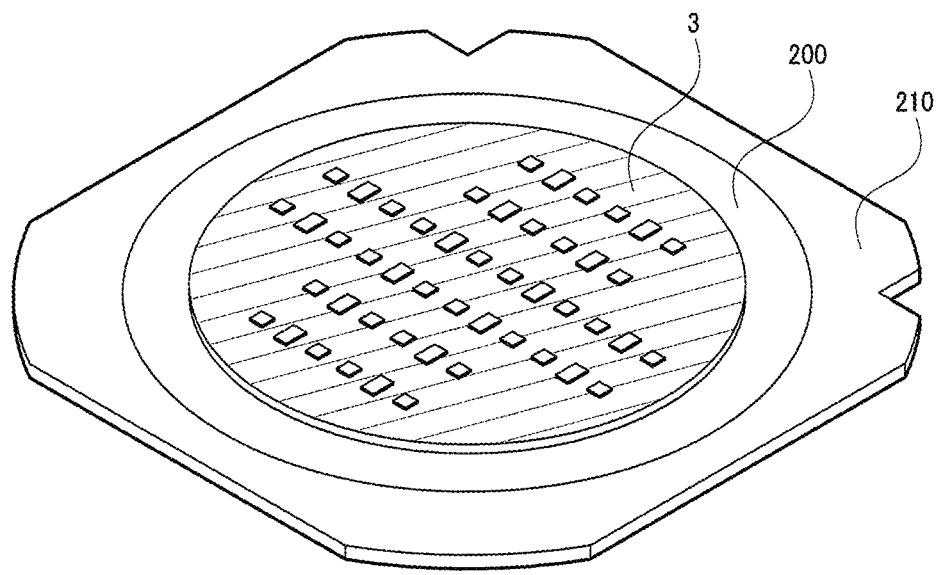
FIGS. 9A and 9B each illustrate a step of singulating the imaging modules by executing wafer dicing process.
Figure 9B:
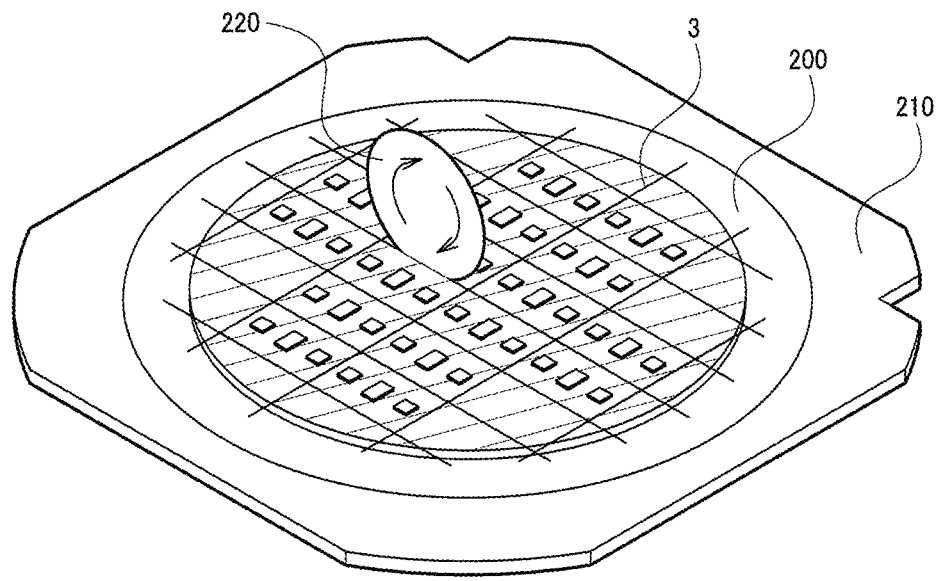

Each of FIGS. 9A and 9B is a perspective view illustrating the singulation step for singulation of the imaging modules 3 in the wafer-like state, which have been produced as illustrated in FIGS. 6A to 8B by the wafer dicing process. The singulation step includes an attachment step of attaching the wafer-like imaging modules 3 to a dicing tape 200, and a dicing step of dicing the wafer-like imaging modules 3.

As illustrated in FIG. 9A, the attachment step is executed by attachment of the wafer-like imaging modules 3 to a position around the center of the dicing tape 200. A dicing ring frame 210 used for transportation or the like is attached to a circumference of the dicing tape 200. The attachment step is executed by the wafer dicing processing device. The attachment step is executed by attachment of the dicing tape 200 to the side of the first surface SF1 of the wafer-like imaging modules 3. The attachment step may also be executed by attachment of the dicing tape 200 to the side of the second surface SF2.

Referring to FIG. 9B, although partially omitted, the dicing step is executed using a dicing blade 220 rotating at high speeds for singulation of the imaging modules 3. The dicing step includes an alignment step of determining a processing position and a processing direction using a prescribed camera.

The alignment step may be executed by recognizing images of alignment marks on the respective points of the imager 30. The alignment step, however, may be executed using other patterns. The alignment step may be executed using a pattern which has been formed based on images of the incidence surface 35 and the front surfaces 11, for example. The alignment step may be executed using a pattern which has been formed based on an image of a surface of the dummy component, for example. The alignment step may be executed using a pattern which has been formed in the fourth step or the fifth step as described above, for example.

The singulation step may be executed by the additional laser machining and expansion for expanding the dicing tape 200, or by combining those techniques.

The singulation step may be executed by the process except the singulation step as illustrated in FIGS. 9A and 9B. For example, the singulation step may be executed by adding the groove forming step to the third step, and further adding a pre-dicing grinding step of grinding until the groove is exposed from the side of the first surface SF1. This makes it possible to clean the incidence surfaces of many imaging modules 3 collectively, and to make the imaging module 3 further thinner.

Japanese Patent Laid-Open No. 2009-240634 discloses manufacturing of wafer-level camera modules. As the camera modules are mounted on the mount substrate one by one, the manufacturing cost cannot be reduced. The method of manufacturing imaging modules 3 according to the embodiment allows formation of the packaged imaging modules in the wafer-like state. This makes it possible to further reduce the manufacturing cost.

The method of manufacturing imaging modules of the embodiment is not limited to the one as described above, but is applicable to the method of manufacturing the imaging modules 3 as described below.

The wafer-like imaging modules 3 bonded to the support substrate 60 described above may be diced.

3. Imaging Module Including Light Guiding Optical Member

The imaging module 3 of the embodiment may be provided with light guiding optical members 70A, 70B (hereinafter, as appropriate, simply referred to as light guiding optical members 70 collectively) each disposed on the incidence surface 35 of the imager 30 for guiding the incident light toward the incidence surface 35, as illustrated by the sectional views of FIGS. 10 and 11. The incident light refers to the one emitted from an object. Codes and explanations given to the structures similar to those described above will be omitted.

Figure 10:
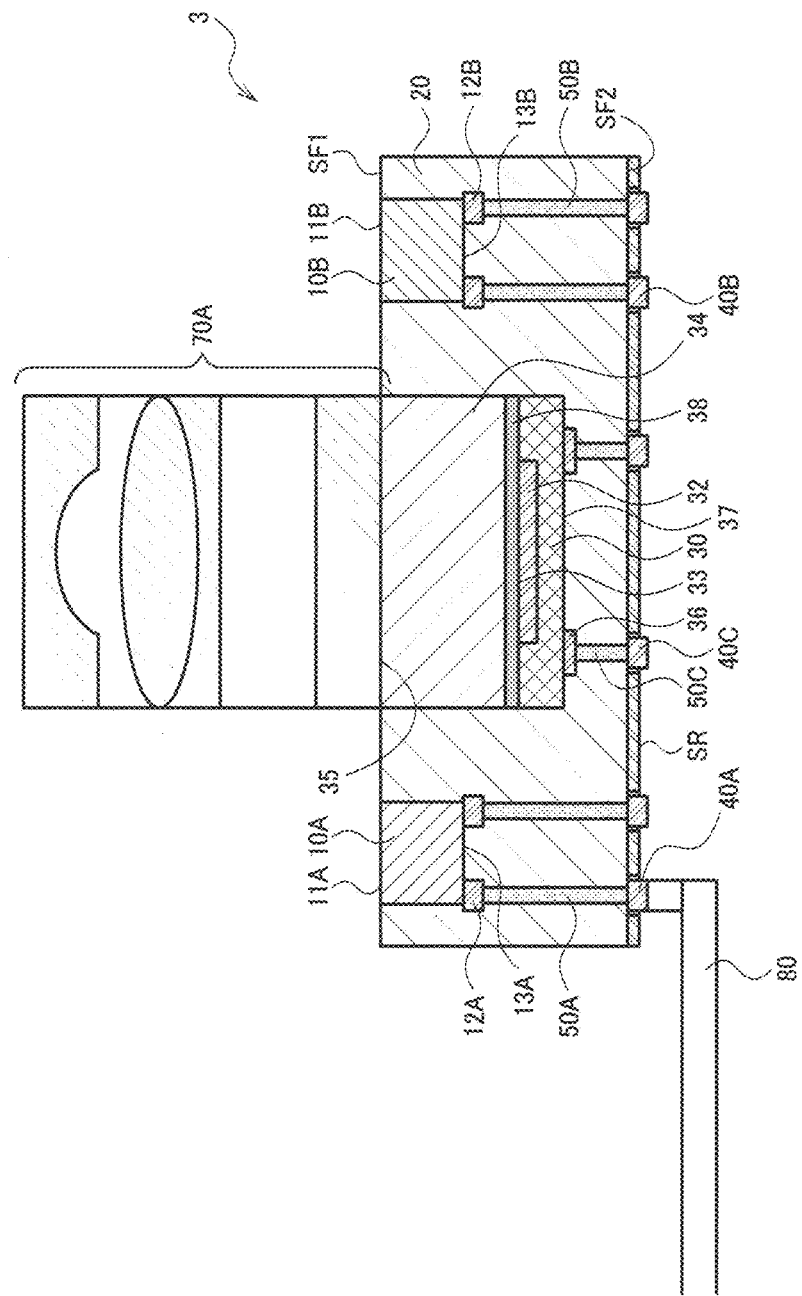
FIG. 10 illustrates a configuration example of an imaging module including a light guiding optical member.

Referring to the imaging module 3 in FIG. 10, the light guiding optical member 70A is bonded to the incidence surface 35 of the imager 30 using a not shown transparent adhesive. The light guiding optical member 70A is formed as a lens unit, for example. Referring to the imaging module 3 in FIG. 10, a cable 80 is connected with one of the external connection terminals 40. However, the cable 80 may be connected to the arbitrary number of external connection terminals 40. Referring to the imaging module 3 in FIG. 10, an optical axis of the light guiding optical member 70A is aligned with a direction orthogonal to the light receiving surface 33 of the imaging element 32.

Figure 11:
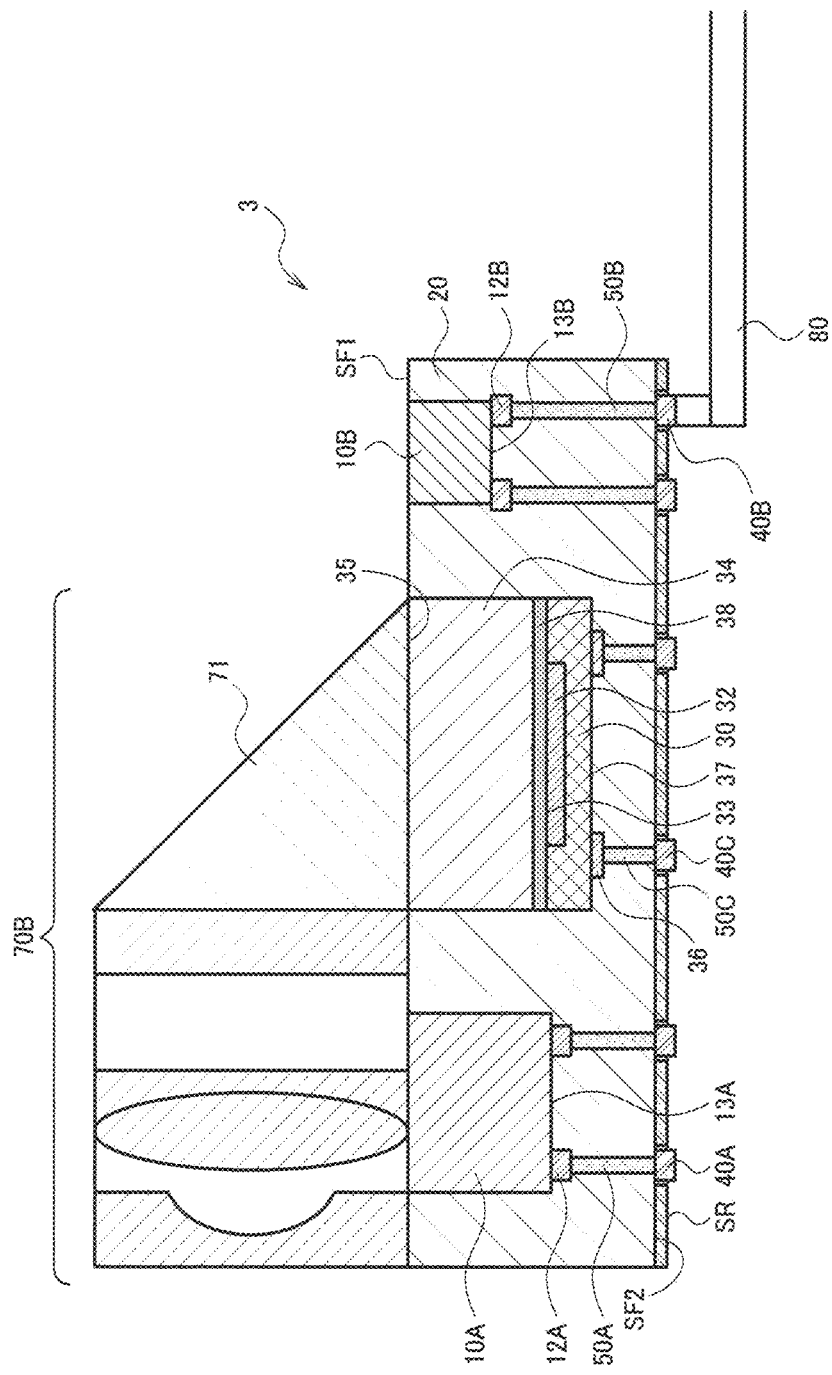
FIG. 11 illustrates a modification of the imaging module including the light guiding optical member.

Referring to FIG. 11, the imaging module 3 is provided with the light guiding optical member 70B which bends the incident light to be guided toward the incidence surface 35. That is, FIG. 10 illustrates that an optical axis of the light guiding optical member 70A is aligned with the direction orthogonal to the light receiving surface 33 of the imaging element 32. Meanwhile, FIG. 11 illustrates that an optical axis of the light guiding optical member 70B extends parallel to the first surface SF1. Specifically, the imaging module 3 as illustrated in FIG. 11 has the light guiding optical member 70B including a prism 71, which is disposed on the incidence surface 35. The imaging module 3 may be configured by connecting the cable 80 to the external connection terminal 40. The process for connection between the external connection terminal 40 and the cable 80 may be variously modified.

Referring to FIGS. 10 and 11, the imaging module 3 has the light guiding optical member 70 for guiding the incident light toward the incidence surface 35, which is disposed on the incidence surface 35 of the imager 30. The use of the light guiding optical member 70 allows the incident light from the object to be guided toward the incidence surface 35 of the imager 30, and the imager 30 to capture an image of the object. The imaging module 3 thus can be incorporated into the endoscope system or the like. The imaging module 3 may be incorporated into the microscope system.

4. Imaging Module Including Multi-Layered Body

Figure 12A:
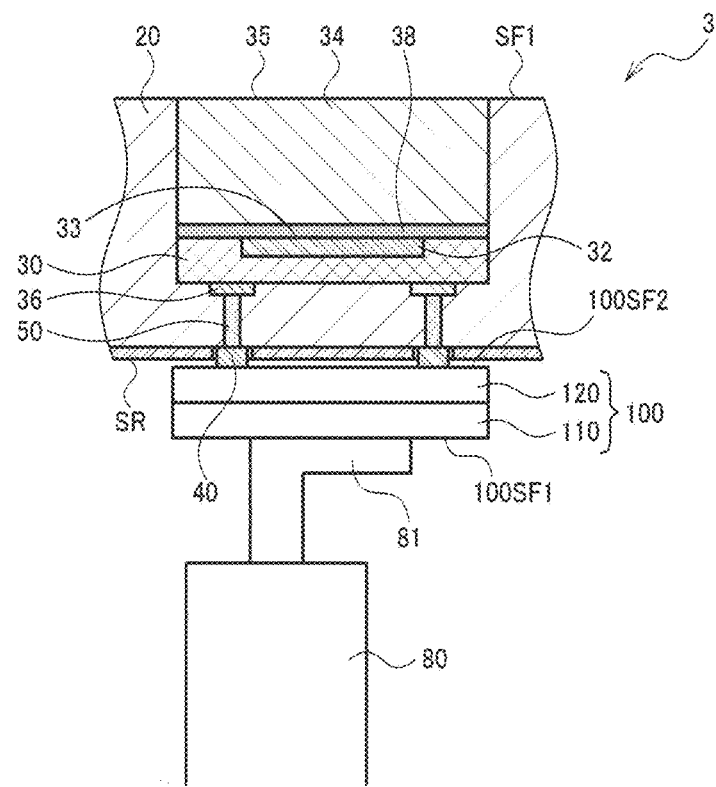
FIGS. 12A and 12B each illustrate a configuration example of an imaging module including a multi-layered body.
Figure 12B:
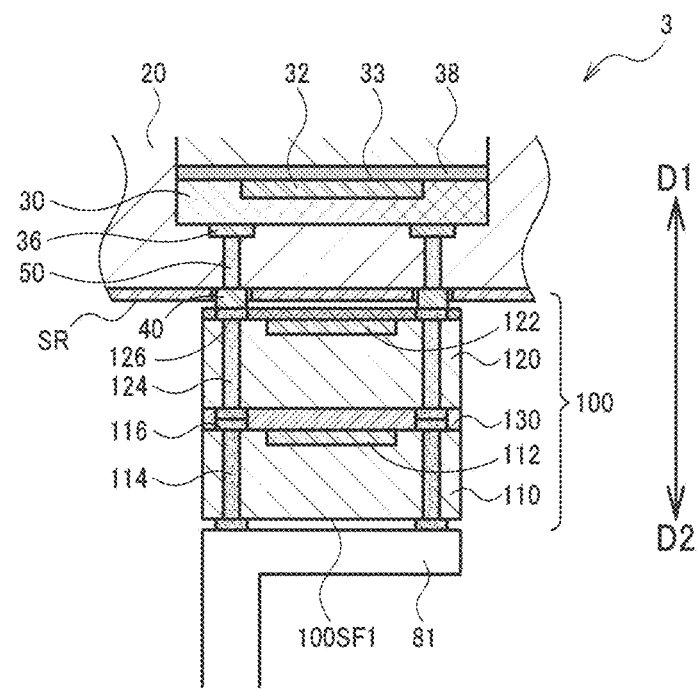

Referring to the imaging module 3 of the embodiment in each sectional view of FIGS. 12A, 12B, a multi-layered body 100 formed by stacking multiple semiconductor elements may be provided on a surface opposite to the light receiving surface 33 of the imager 30. Codes and explanations given to the structures similar to those described above will be partially omitted. The explanation with respect to the electronic components 10 will be omitted.

The multi-layered body 100 is formed by stacking multiple semiconductor elements. The multi-layered body 100 is manufactured by singulation of not shown stacked semiconductor wafer. That is, the multi-layered body 100 is formed by executing the semiconductor wafer process.

Provision of the compact multi-layered body 100 to the packaged imager 30 compact in size synergistically allows the imaging module 3 to be easily incorporated into the endoscope system.

The multi-layered body 100 as illustrated in FIG. 12A is constituted as a double-layered structure including a first semiconductor layer 110 and a second semiconductor layer 120. It may also be constituted by three or more layers of semiconductor elements.

The multi-layered body 100 is connected to the cable 80 which intervenes between the multi-layered body 100 and the external device. However, the connection may be attained in various modifications. For example, as illustrated in FIG. 12A, the multi-layered body 100 and the cable 80 may be connected via a flexible printed board 81 on a surface 100SF1 opposite to a surface 100SF2 of the multi-layered body 100 to be connected with the external connection terminal 40.

FIG. 12B illustrates a detailed configuration of the multi-layered body 100. In the description below, a code D1 denotes a direction toward the light receiving surface 33 from a back surface thereof, and a code D2 denotes a direction opposite to the direction D1. For example, as illustrated in FIG. 12B, the first semiconductor layer 110, the second semiconductor layer 120, and the imager 30 are stacked in this order along the direction D1.

The first semiconductor layer 110 and the second semiconductor layer 120 are stacked via a sealing resin layer 130. The first semiconductor layer 110 and the second semiconductor layer 120 have through-vias 114 and 124, respectively. The first semiconductor layer 110 and the second semiconductor layer 120 are connected with a layer adjacent to the multi-layered body 100 or the imager 30 via the through vias 114, 124, and bumps 116, 126, respectively. For example, referring to an example illustrated in FIG. 12B, the second semiconductor layer 120 is connected with the imager 30, and the first semiconductor layer 110 is connected to the second semiconductor layer 120. A first semiconductor element 112 is disposed on a surface of the first semiconductor layer 110 at the side D1. A second semiconductor element 122 is disposed on a surface of the second semiconductor layer 120 at the side D1. The first semiconductor element 112 may be disposed on a surface of the first semiconductor layer 110 at the side D2, or both sides. Correspondingly, the second semiconductor element 122 may be disposed on a surface of the second semiconductor layer 120 at the side D2, or both sides.

The configuration of the imaging module 3 including the multi-layered body 100 is not limited to those illustrated in FIGS. 12A, 12B. The configuration may be variously modified by omitting a part of those components or adding other components.

Figure 13:
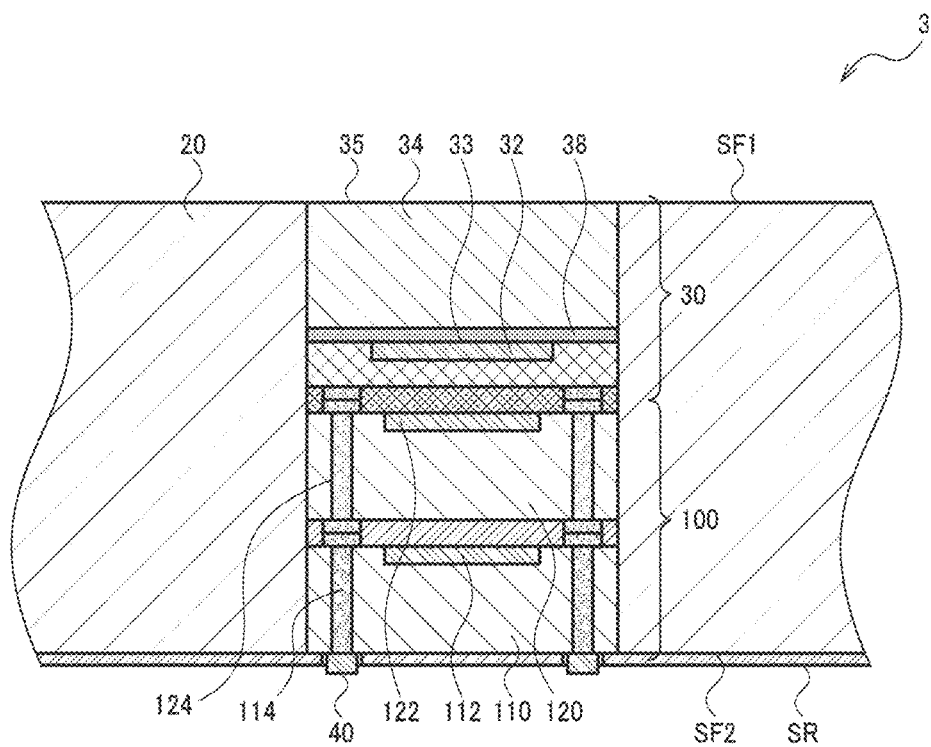
FIG. 13 illustrates a configuration example of an imaging module in which the multi-layered body is included in a resin portion.

The imaging module 3 of the embodiment may be configured to embed the imager 30 and the multi-layered body 100 in the resin portion 20 as the sectional view in FIG. 13 illustrates. Codes and explanations given to the structures similar to those described above will be partially omitted. The explanation with respect to the electronic components 10 will be omitted.

The imaging module 3 has the imager 30 and the multi-layered body 100 firmly fixed with the resin portion 20 to allow improvement in reliability. It is also possible to simplify the process of manufacturing the endoscope or the like.

5. Imaging Module Containing Light Guiding Optical Member in Resin Portion

Figure 14:
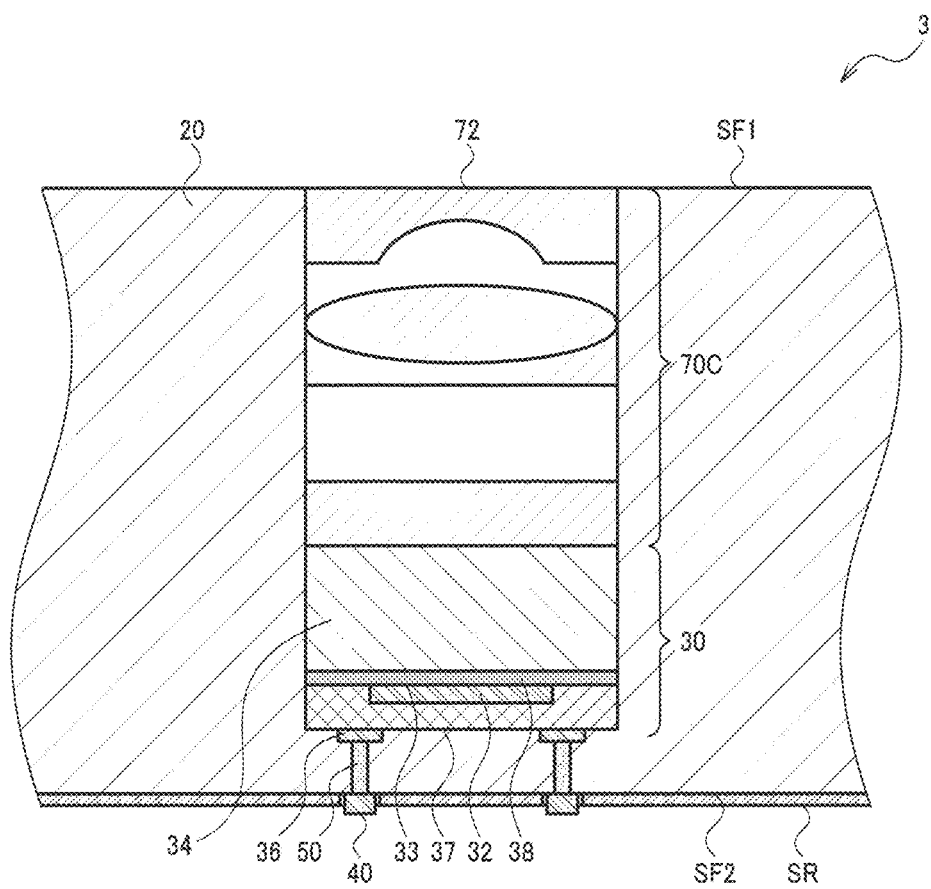
FIG. 14 illustrates a configuration example of an imaging module in which the light guiding optical member is included in the resin portion.

As the sectional view in FIG. 14 illustrates, the imaging module 3 of the embodiment may be provided with a light guiding optical member 70C inside the resin portion 20. Codes and explanations given to the structures similar to those described above will be omitted. The explanation with respect to the electronic components 10 will be omitted. Referring to FIGS. 10 and 11, the light guiding optical members 70A, 70B are disposed on the incidence surface 35 exposed to the first surface SF1 of the resin portion, respectively. Referring to FIG. 14, the light guiding optical member 70C bonded to the optical member 34 is sealed with resin so that a light guiding incidence surface 72 of the light guiding optical member 70C is exposed to the first surface SF1.

The imaging module 3 has the imager 30 and the light guiding optical member 70C firmly fixed to allow improvement in reliability. It is also possible to simplify the process of manufacturing the endoscope or the like.

6. Imaging Module Including Shielding Member

Figure 15A:
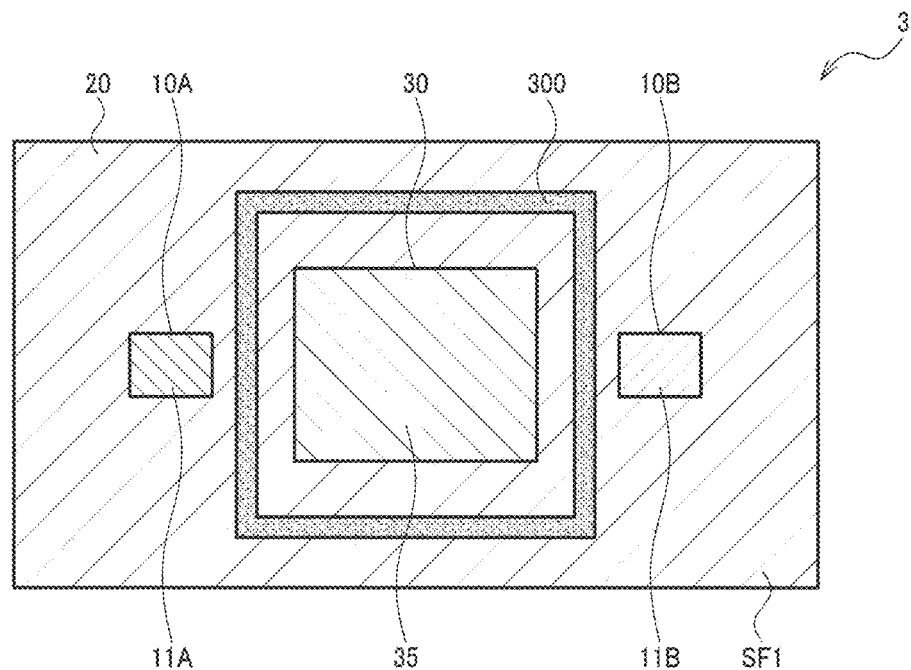
FIGS. 15A and 15B each illustrate a configuration example of an imaging module including a shielding member.
Figure 15B:
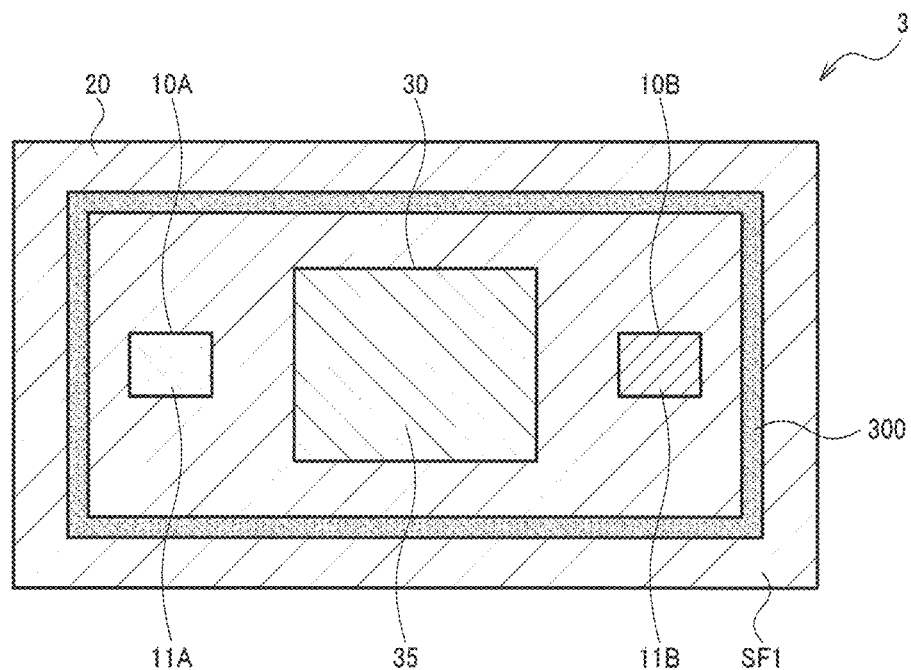

The imaging module 3 of the embodiment may be provided with a shielding member 300 for enclosing at least the imager 30. FIGS. 15A, 15B are plan views each illustrating a configuration example of the imaging module 3 including the shielding member 300 in a planar view in the direction vertical to the first surface SF1. Codes and explanations given to the structures similar to those described above will be omitted.

As illustrated in FIGS. 15A, 15B, the shielding member 300 may be formed to extend from the first surface SF1 to the second surface SF2, or extend from either the first surface SF1 or the second surface SF2 to the middle of the depth. That is, the shielding member 300 may be formed to positionally overlap at least with the imager 30 in a side view from the direction orthogonal to the vertical direction of the first surface SF1.

Referring to the imaging module 3 in FIG. 15A, the shielding member 300 is formed to enclose only the imager 30. Like the imaging module 3 in FIG. 15B, the shielding member 300 may be formed to enclose the imager 30 and the electronic components 10. Although not shown, the shielding member 300 may be formed to enclose the imager 30 and an arbitrary one of the electronic components 10.

The shielding member 300 may be formed using the same material as the one for forming the through wiring 50, or using the different material from the one for forming the through wiring 50. The shielding member 300 is produced in the step other than the third and the fourth steps as described above. However, it may be formed along with the third and the fourth steps. Accordingly, those manufacturing steps can be integrated.

The foregoing imaging module 3 allows the imager 30 and the electronic components 10 to be shielded from noise and stray light.

7. Imaging Module Including Opening

Figure 16A:
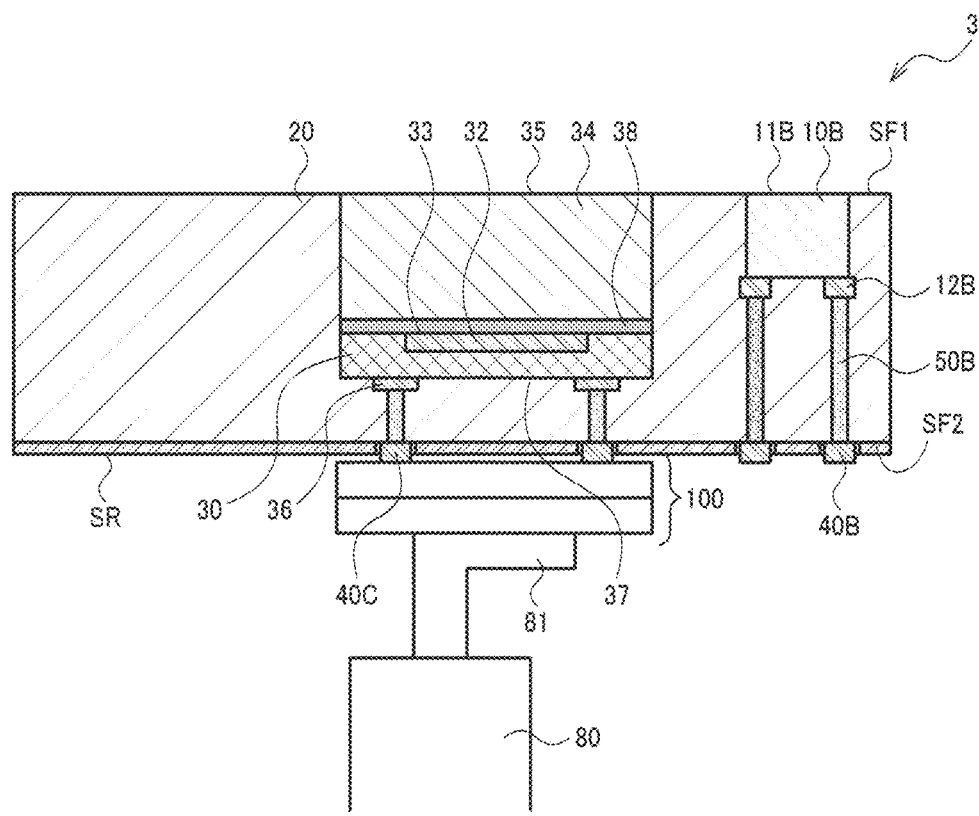
FIGS. 16A and 16B each illustrate a configuration example of an imaging module having an opening.
Figure 16B:
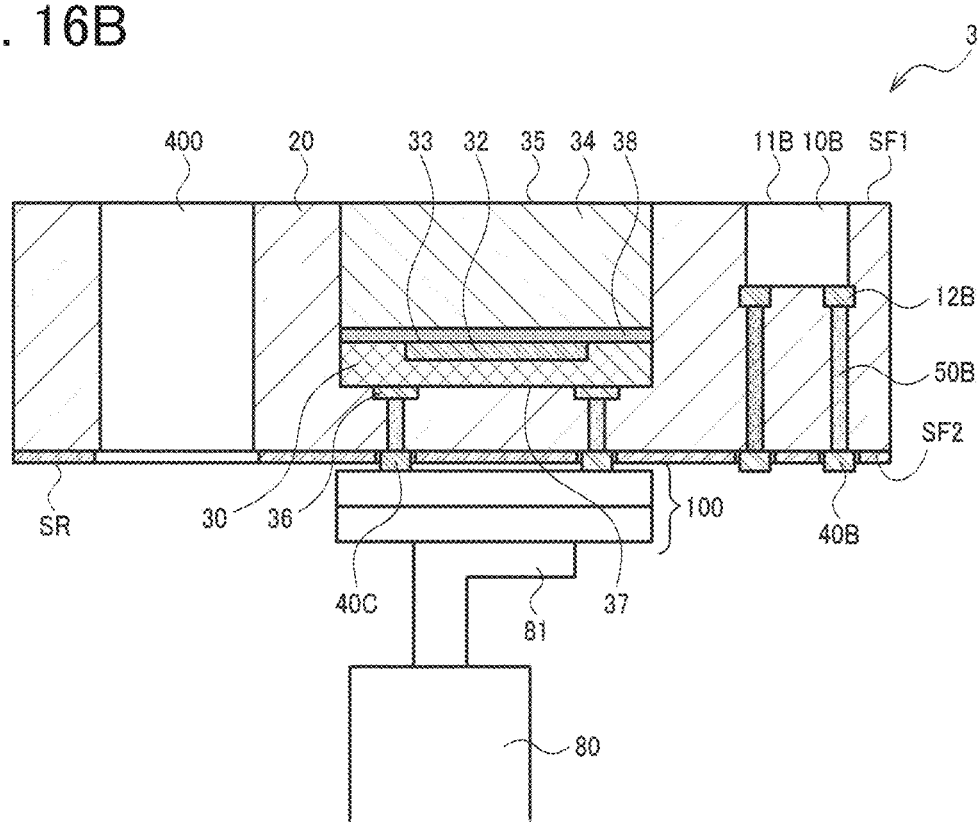

As the sectional view in FIG. 16B illustrates, the imaging module 3 of the embodiment may be configured to form an opening 400 in the resin portion 20, which extends from the first surface SF1 to the second surface SF2. Codes and explanations given to the structures similar to those described above will be omitted. For example, the opening 400 is formed by laser machining, or may be formed by etching. The through hole 54 as illustrated in FIG. 7A is formed for conduction by the through wiring 50. Meanwhile, the opening 400 is formed to serve as a water feed hole or a forceps hole for the endoscope. The opening 400 is formed by executing the process separately from the third step as described above. However, it may be formed along with the third step. Accordingly, those manufacturing steps can be integrated. The imaging module 3 as illustrated in FIGS. 16A, 16B includes the multi-layered body 100 as described above. The imaging module 3 may also be manufactured without including the multi-layered body 100.

8. Endoscope System

The method according to the embodiment is applicable to an endoscope system. An endoscope system 2 includes the above-described imaging module 3, and a processor 75A for processing image data acquired by the imaging module 3. The imaging module 3 includes the imager 30, the electronic components 10, the resin portion 20, and the external connection terminals 40. As the imager 30, the electronic components 10, the resin portion 20, and the external connection terminals 40 have been described above in detail, explanations thereof thus will be omitted. Specifically, the endoscope system 2 is configured as illustrated in FIG. 17.

The endoscope system 2 includes an endoscope 1 including the imaging module 3, and the processor 75A for processing the image data acquired by the imaging module 3. Specifically, the endoscope 1 includes an insertion portion 73, a grip portion 74 disposed at a base end of the insertion portion 73, a universal code 74B extending from the grip portion 74, and a connector 74C disposed at a base end of the universal code 74B. The insertion portion 73 includes a rigid top end portion 73A to which the imaging module 3 is attached, a bending portion 73B extending from a base end of the top end portion 73A, which is bendable for changing the direction of the top end portion 73A, and a flexible portion 73C extending from a base end of the bending portion 73B. The grip portion 74 includes a rotatable angle knob 74A as an operation portion which allows an operator to operate the bending portion 73B. The endoscope system 2 may be configured to include a display device 75B for displaying the image processed by the processor 75A.

In the embodiment, the top end portion 73A includes the imaging module 3 and a housing. However, the top end portion 73A may be constituted only by the imaging module 3.

Figure 17:
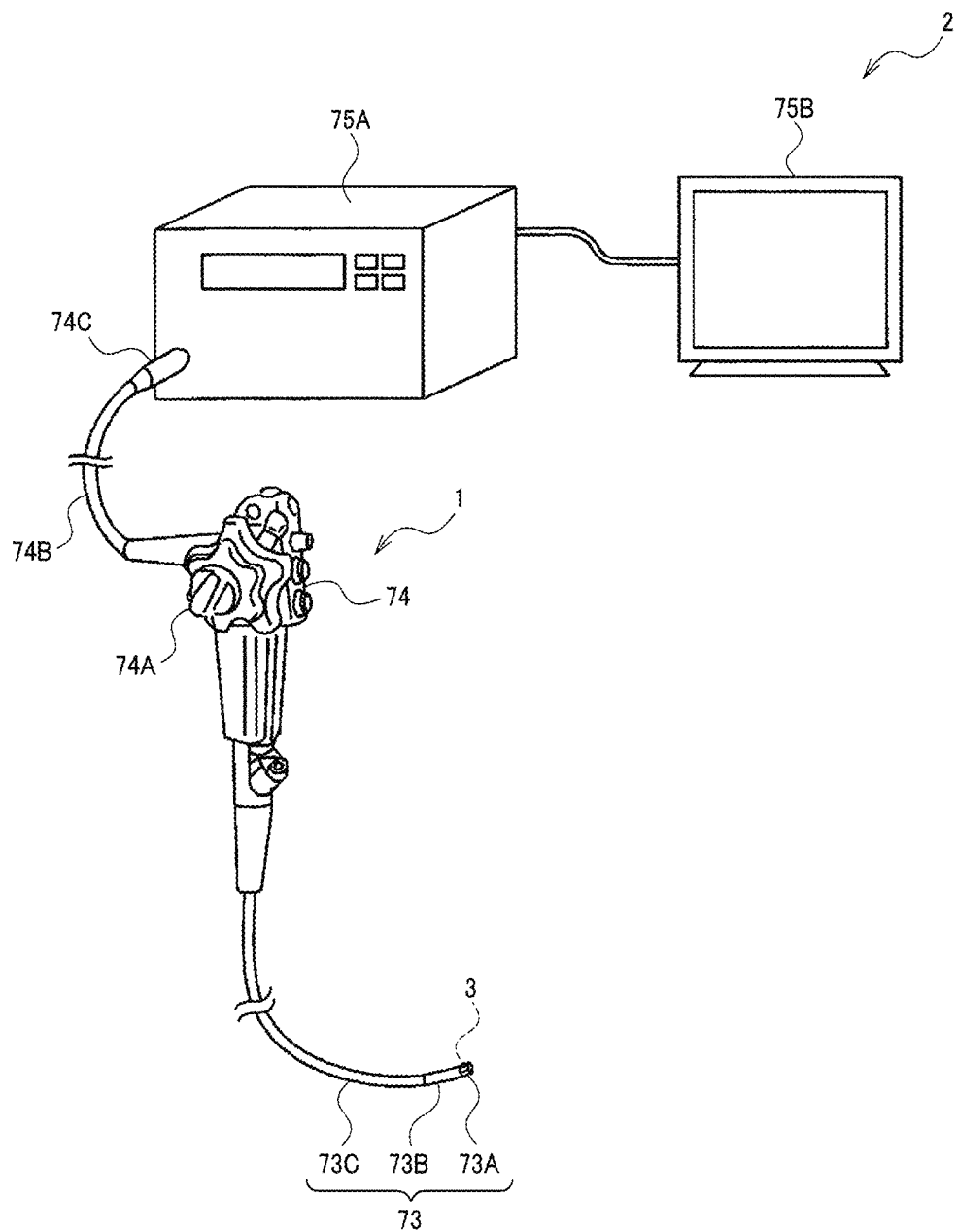
FIG. 17 illustrates a configuration example of an endoscope system including an imaging module.

The endoscope system 2 of the embodiment is not limited to the one as illustrated in FIG. 17, but is applicable to various types of endoscope systems. For example, like the capsule type endoscope, the endoscope system may be configured to attain wireless communication between the top end portion 73A and the processor 75A. The endoscope system 2 of the embodiment may also be configured to allow the external server or the like to control the endoscope 1, or allow AI to operate the endoscope 1.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:
1. An imaging module, comprising:
   an imager having an optical member on a light receiving surface;
   an electronic component having a front surface, the front surface and an incidence surface of the optical member facing a same direction;
   a resin portion that has a first surface flush with the incidence surface of the optical member and the front surface of the electronic component, and a second surface that is a surface on a side opposite to the first surface, the imager and the electronic component being embedded in the resin portion such that the incidence surface and the front surface are exposed to the first surface;
an external connection terminal provided on the second surface; and
a through wiring that extends through the resin portion to connect at least one of the imager and the electronic component with the external connection terminal.

2. The imaging module as defined in claim 1, wherein the through wiring connects the external connection terminal with one of the imager and the electronic components selectively in accordance with a distance from the second surface to each surface of the imager and the electronic components on a side opposite to the second surface, whichever is the longest.

3. The imaging module as defined in claim 1, further comprising a rewiring formed on the second surface for connecting at least one of a connection terminal of the imager, a connection terminal of the electronic component, and the through wiring with the external connection terminal.

4. The imaging module as defined in claim 1, wherein at least one of a connection terminal of the imager and a connection terminal of the electronic component is exposed from the second surface to serve as the external connection terminal.

5. The imaging module as defined in claim 1, wherein the optical member is a cover glass that protects the light receiving surface.

6. The imaging module as defined in claim 5, further comprising a light guiding optical member provided on the incidence surface of the imager to guide an incident light toward the incidence surface.

7. The imaging module as defined in claim 1, further comprising a multi-layered body disposed on a surface opposite to the light receiving surface of the imager, the multi-layered body including multiple layers formed by stacking multiple semiconductor elements.

8. The imaging module as defined in claim 1, wherein the optical member is a lens unit formed by stacking multiple optical elements including a cover glass.

9. The imaging module as defined in claim 1, wherein the electronic component includes an active element.

10. The imaging module as defined in claim 1, wherein the electronic component is a light emitting element.

11. The imaging module as defined in claim 1, further comprising a shielding member that encloses at least the imager in a planar view from a vertical direction to the first surface, the shielding member being formed to positionally overlap at least with the imager in a side view from a direction orthogonal to a vertical plane of the first surface.

12. The imaging module as defined in claim 1, wherein the resin portion has an opening extending through the resin portion from the first surface to the second surface.

13. An endoscope system including an imaging module and a processor that processes image data acquired by the imaging module, wherein:
the imaging module includes:
an imager having an optical member on a light receiving surface;
an electronic component having a front surface, the front surface and an incidence surface of the optical member facing a same direction;
a resin portion that has a first surface flush with the incidence surface of the optical member and the front surface of the electronic component, and a second surface that is a surface on a side opposite to the first surface, the imager and the electronic component being embedded in the resin portion such that the incidence surface and the front surface are exposed to the first surface;
an external connection terminal provided on the second surface; and
a through wiring that extends through the resin portion to connect at least one of the imager and the electronic component with the external connection terminal.

14. An imaging module manufacturing method comprising:
a mounting step of mounting an imager and an electronic component on a support substrate such that both an incidence surface of the imager and a front surface of the electronic component face the support substrate;
a sealing step of supplying a resin onto the support substrate to seal the imager and the electronic component to form a resin portion having a first surface and a second surface on a side opposite to the first surface, the first surface being flush with the incidence surface of the imager and the front surface of the electronic component; and
a removing step of removing the support substrate.

15. The imaging module manufacturing method as defined in claim 14, further comprising a through wiring forming step of forming a through wiring in the resin portion for connection with at least one of the imager and the electronic component from the second surface.

16. The imaging module manufacturing method as defined in claim 14, wherein in the sealing step, the resin portion is formed such that at least one of a connection terminal of the imager and a connection terminal of the electronic component is exposed from the second surface to serve as an external connection terminal.

17. The imaging module manufacturing method as defined in claim 14, wherein the mounting step, the sealing step, and the removing step are executed to form multiple units of the imaging modules collectively in a wafer-like state, the imaging module manufacturing method further comprising a singulation step of singulating the multiple imaging modules by executing a wafer dicing process.

* * * * *